United States Patent [19]

Bornstein et al.

[11] 4,146,971
[45] Apr. 3, 1979

[54] METHOD OF PREPARING A RAPIDLY DISSOLVING POWDER OF STERILE CRYSTALLINE CEFAZOLIN SODIUM FOR PARENTERAL ADMINISTRATION

[75] Inventors: Michael Bornstein; Michael D. Cise, both of Indianapolis, Ind.

[73] Assignee: Eli Lilly and Company, Indianapolis, Ind.

[21] Appl. No.: 860,365

[22] Filed: Dec. 14, 1977

Related U.S. Application Data

[63] Continuation-in-part of Ser. No. 744,552, Nov. 24, 1976, abandoned.

[51] Int. Cl.$^2$ ............................................. F26B 5/06
[52] U.S. Cl. ................................................... 34/5
[58] Field of Search .......................................... 34/5

[56] References Cited

U.S. PATENT DOCUMENTS 3,449,885  6/1969  Starkey ................................. 34/5 X
4,029,655  6/1977  Cise ................................. 424/246 X

FOREIGN PATENT DOCUMENTS 2362785  6/1975  Fed. Rep. of Germany ................ 34/5

*Primary Examiner*—John J. Camby
*Attorney, Agent, or Firm*—Arthur R. Whale; Ralph W. Ernsberger

[57] ABSTRACT

Sterile, essentially crystalline cefazolin sodium for parenteral administration is prepared by a freeze-drying process wherein a $C_1$-$C_3$ alcohol-water solution of cefazolin sodium containing about 10 percent by volume of the $C_1$-$C_3$ alcohol is chilled slowly from room temperature to about $-10°$ C. over a 3-12 hour period and then rapidly cooled to $-30°$ to about $-40°$ C. and held for 1-2 hours before subjecting said frozen solution to a high vacuum and a moderate amount of heat to sublime the frozen solvent therefrom. The resulting powder dissolves rapidly in acceptable pharmaceutical diluents.

13 Claims, No Drawings

METHOD OF PREPARING A RAPIDLY DISSOLVING POWDER OF STERILE CRYSTALLINE CEFAZOLIN SODIUM FOR PARENTERAL ADMINISTRATION

CROSS-REFERENCE

This application is a continuation-in-part of copending application Ser. No. 744,552 filed Nov. 24, 1976, now abandoned.

BACKGROUND OF THE INVENTION

1. Field of Invention

This invention is directed to an improved freeze-drying (lyophilization) process. More specifically the instant invention concerns a freeze-drying process wherein cefazolin sodium for parenteral administration is prepared which is sterile, essentially crystalline and is rapidly soluble on reconstitution in a conventional acceptable pharmaceutical diluent.

2. Prior Art

Freeze-drying is an old and often used process for removing a solvent from a solute. While the process is cumbersome, expensive and slow, it provides a method for removing a solvent without damaging heat labile solutes. Antibiotics and other pharmaceuticals have been processed by freeze-drying procedures for three or more decades and foods, particularly instant coffee, have been prepared by this method for many years. Ordinarily, a solution from which it is desired to recover the solute in a relatively solvent-free state is frozen solid and then subjected to an environment of a high vacuum, and the temperature of the environment is raised to provide the units of heat absorbed in the sublimation of the frozen solvent. The temperature of the environment is kept below that which would result in the meltdown of the frozen solution. In practice, the temperature of the environment is coordinated with the vacuum to produce the highest reasonable sublimation rate, avoiding a melting of the frozen mass.

Water is the solvent generally utilized in a freeze-drying process. Other solvents of combinations thereof can be employed but are limited to those which become solid in the range of temperatures which can be employed practically in the process and which will sublime under vacuum.

Although all of the material does not have to be in solution to effectively operate a freeze-drying process, instant coffee being one probable example, this invention is concerned with a process wherein crystalline cefazolin sodium is prepared in a freeze-drying procedure from a true solution. In freeze-drying antibiotics and other pharmaceuticals it has been the practice to follow the classic process outlined above; to wit, prepare solution, freeze to solid, subject to high vacuum, add heat, sublime solvent. However, when such a conventional procedure is followed, cefazolin sodium comes out as a slowly soluble powder.

The cefazolin sodium involved in this invention can be recovered from organic solvents, such as ethanol, in an essentially crystalline state. The crystals are equally as stable as the crystals prepared by the freeze-drying process of the instant invention.

However, recovering crystals of cefazolin sodium for use in sterile ampoule preparations for parenteral administration poses other problems and conditions which are both inefficient, difficult and costly. For example, there is no effective way known to sterilize the crystals of cefazolin sodium recovered from organic solvents so the entire crystallization process must be carried out in an aseptic environment. In the large and extensive process required to sterilely crystallize cefazolin sodium there are many opportunities for the admittance of foreign materials into the crystals which later on will show up as particulate matter in a reconstituted ampoule of the antibiotic. No one has yet developed an apparatus for filling dry material into an ampoule which will measure the material going into each ampoule with as good a consistency and precision as can be routinely achieved with liquid filling equipment.

U.S. Pat. No. 4,029,655 teaches and claims a novel and useful freeze-drying process for preparing crystalline cefazolin sodium for parenteral administration. The process embodies a procedure which includes a very rapid cooling of an aqueous solution to nucleate the cefazolin sodium during the interval that the freezing takes place. Such nucleation crystallizes the bulk of the cefazolin sodium from the solution immediately prior to the solidification of the water. Consequently, when the sublimation procedure is initiated the cefazolin sodium already exists as crystals and does not depend on the crystallization to take place as the solvent is removed. The solvent is sublimed away and the cefazolin sodium remains behind.

While the process provides a means for obtaining stable sterile crystalline cefazolin sodium for parenteral administration, the resulting crystals do not dissolve rapidly in acceptable pharmaceutical diluents. Generally, two minutes or more of vigorous shaking is required to reconstitute such cefazolin sodium in a solution appropriate for injection. The relatively long time is a source of annoyance and irritation to nurses, technicians and physicians who are called on to prepare the injectable solution prior to administration. Cefazolin sodium, the substance involved in the instant invention is in use today for combatting susceptible pathological organisms in sick people.

Accordingly, it is an object of this invention to provide a process of freeze drying cefazolin sodium that will result in sterile essentially crystalline powder for reconstitution for parenteral administration having a rapid dissolving characteristic in acceptable pharmaceutical diluents.

Another object of this invention is to provide a process which will include the sterile liquid filling of a measured volume of a sterile solution of a known concentration of cefazolin sodium into an ampoule wherein such cefazolin sodium is recovered from such solution as an essentially crystalline material for reconstitution for parenteral administration which is storage stable.

Still another object of this invention is to provide an ampoule containing an essentially crystalline cefazolin sodium which is storage stable and which upon reconstitution for parenteral administration is substantially free of foreign particulate matter.

SUMMARY

Now it has been discovered that a storage stable, sterile, essentially crystalline cefazolin sodium for reconstitution for parenteral administration can be prepared by a freeze-drying procedure comprising the following steps: (a) Cefazolin sodium is dissolved in a solvent system comprised of from about 2 to about 25 percent of a $C_1$–$C_3$ alcohol and from about 98 to about 75 percent water (v/v) in a concentration of between about 20 and about 40 percent (w/v). (b) The cefazolin sodium preparation from (a) is sterile filtered into a previously sterilized container. (c) The cefazolin sodium preparation from (b) is slowly cooled to a temperature of about −10° C. within an interval of from 3–12 hours. (d) The temperature of the cefazolin sodium preparation from (c) is then rapidly cooled to between −30° C. and about −40° C. until it has completely solidified. (e) The cefazolin sodium preparation from (d) is held below −30° C. for 1–2 hours. (f) The cefazolin sodium preparation from (e) is subjected to an environment in which the pressure is maintained at a maximum of 1 mm absolute. And, (g) the temperature of the environment in which the cefazolin sodium preparation from (f) is maintained at a maximum of 1 mm absolute is raised to 50° C. or below, subliming the solvent from the cefazolin sodium preparation resulting in the recovery of an essentially crystalline cefazolin sodium having a moisture content of not more than 6.0 percent, and a $C_1$–$C_3$ alcohol content of not more than 1.0 percent.

DESCRIPTION OF THE PREFERRED EMBODIMENTS

The useful process of the present invention comprises a procedure utilizing a freeze-drying operation wherein from about 20 to about 40 percent (w/v) of cefazolin sodium is dissolved in a solvent system comprised of from about 2 to about 25 percent of a $C_1$–$C_3$ alcohol and from about 98 to about 75 percent water. Such a solution is then sterilized by filtration. The sterile solution is then exposed to an environment in which the solution is cooled slowly from room temperature to a temperature of about −10° C. The cooling period should extend over from 3 to about 12 hours during which time upwards of about 50 percent or more of the dissolved cefazolin sodium is crystallized from the solution before any freezing begins.

After the slow cooling to about −10° C. over the 3–12 hour period, the cooled solution is rapidly chilled to between −30° and about −40° C. and held at such temperature for from 1 to 2 hours to assure complete freezing.

Following the critical steps just described, a conventional freeze-drying operation is employed to sublime the ice, leaving sterile cefazolin sodium crystals having a moisture content of not more than 6 percent and a $C_1$–$C_3$ alcohol content of not more than 1 percent. Such crystals have a suitable storage stability of three years or more at room temperature, and dissolve in one minute or less in an acceptable pharmaceutical diluent in concentrations appropriate for parenteral administration. The improvement in the solubility characteristics of the cefazolin sodium prepared by the process described above over the conventionally prepared cefazolin sodium crystals freeze-dried from an aqueous solution results in about a 50 percent reduction in the reconstiution time of the cefazolin sodium in an acceptable pharmaceutical diluent.

The $C_1$–$C_3$ alcohols used in this process include methanol, ethanol, n-propanol and isopropanol and mixtures thereof. Denatured ethanols may also be utilized providing the denaturing agent is pharmaceutically acceptable and volatile. Ethanol and the denatured ethanols are the preferred alcohols used in this invention.

The crux of the instant invention is found in the combination of the use of the $C_1$–$C_3$ alcohol-water solvent system and the slow cooling of a solution of cefazolin sodium contained in such a solvent system to a temperature of about −10° C. The presence of the $C_1$–$C_3$ alcohol in the solvent system allows for the chilling of the solution to about −10° C. without the formation of ice therein. It was discovered that the cefazolin sodium is substantially less soluble in a $C_1$–$C_3$ alcohol-water solvent than in water alone. Consequently, at the −10° C. temperature upwards of about 50 percent or more, depending on the concentration of the solute, of the cefazolin sodium is crystallized from solution before ice begins to form. Moreover, by slowly reducing the temperature of the solution from room to −10° C., the resulting crystals are large with a small surface area when compared to the crystals obtained from the freeze-drying of cefazolin sodium by conventional procedures.

Once ice begins to form, the temperature of the solution is reduced rapidly to favor the development of dendritic ice promoting the nucleation of the cefazolin sodium remaining in solution. As the concentration of the cefazolin sodium remaining in solution when the actual solidification of the solution is initiated is significantly lowered, as related to conventional freeze-drying methods employing aqueous solutions, the crystals which form as the nucleation proceeds are large with small surface area. In actual practice the temperature of the solution is lowered to between −30° C. and about −40° C. and held for 1–2 hours to assure complete freezing.

In one aspect of the present invention a rapidly soluble, sterile, essentially crystalline, cefazolin sodium for reconstitution for parenteral administration is prepared by a method comprised of the following steps: (a) Cefazolin sodium is dissolved in a $C_1$–$C_3$ alcohol-water solvent. (b) The cefazolin sodium solution from (a) is filtered through a sterilizing filter into a previously sterilized container. (c) The preparation from (b) is slowly cooled from room temperature to about −10° C. over a period from 3 to about 12 hours. (d) The preparation from (c) is cooled as rapidly as possible to a temperature of from −30° C. to about −40° C. (e) The preparation from (d) is held at the temperature achieved in (d) for from 1–2 hours. (f) The preparation from (e) is subjected to an environment wherein the pressure is maintained at a maximum of no more than 1mm absolute. (g) The temperature of the environment at which the preparation from (f) is exposed is raised to a maximum of about 50° C., avoiding the melting of such preparation. And, (h) the frozen solvent is sublimed from the preparation from (g) until the resulting crystals of cefazolin sodium have a moisture content of not more than 6 percent, and a $C_1$–$C_3$ alcohol content of not more than 1 percent.

Preferably the $C_1$–$C_3$ alcohol-water solvent employed in the useful method of this invention can contain from about 2 to about 15 percent by volume of a $C_1$–$C_3$ alcohol and from about 98 to about 85 percent water. The especially preferred solvent system is comprised of about 10 percent by volume of ethanol and about 90 percent by volume of water. In practice the cefazolin sodium is dissolved in the water and a volume of 95 percent ethanol equal to about 10 percent of the volume of the aqueous solution of the cefazolin sodium is added to such solution.

A concentration of cefazolin sodium of from about 20 to about 40 percent W/V in the $C_1$–$C_3$ alcohol-water solvent is satisfactory for developing the large crystals on freeze-drying. The preferred range is from about 23 to 28 percent W/V. In practice, one especially preferred concentration of cefazolin sodium is provided by dissolving 1 gm of cefazolin sodium in water q. s'd. to 4 ml and adding thereto 0.4 ml of 95 percent grain alcohol, making a solution containing about 25 percent (W/V) of the solute.

The sterilization of a $C_1$–$C_3$ alcohol-water solution of cefazolin sodium can be achieved by filtering such solution through sterile filtering means known to those skilled in the art and collecting the filtrate in a previously sterilized container. Illustratively, sterile filtering can be effected using a heat sterilized plate and frame filter press equipped with an asbestos pad, or a filtering membrane of cellulose acetate or nitrate, or a candle having a porosity below 0.22 μm.

The slow cooling of the $C_1$–$C_3$ alcohol-water solution of cefazolin sodium can be best accomplished by exposing such solution to an environment of about 15° C. and slowly lowering such temperature about 4° C. every thirty minutes until the actual temperature of the solution is established at about −10° C. The temperature of the solution can be determined by locating a thermocouple approximately in the center of the solution to indicate the temperature at that point. Continued experience with the actual apparatus used to accomplish the lowering of the temperature will provide more useful information as to the operating characteristics which should be followed to meet the processing parameters specified. This is so because of the wide variation in the design and operation of different freeze-dryers.

When the −10° C. temperature has been reached following the method outlined above, the solution should be cooled as rapidly as possible to between −30° C. and about −40° C. There appears to be no benefit in lowering the temperature below −40° C. Once the temperature of the frozen mass of the cefazolin sodium solution reaches −30° C. or below, the temperature should be maintained at that level for at least 1 hour. In practice a 1 to 2 hour period is specified. No apparent benefit was found in holding the frozen mass at less than −30° C. for more than 2 hours. This is done to assure complete freezing. At this point essentially all of the cefazolin sodium is present in the frozen mass as free crystals.

After the nucleation of the cefazolin sodium crystals is substantially complete, a conventional freeze-drying operation is utilized to sublime the solvent from the frozen mass leaving a deposit of sterile, essentially crystalline cefazolin sodium.

The cefazolin sodium preparation wherein the nucleation of the crystals is substantially complete is subjected to an environment where the pressure can be reduced to a practical maximum of no more than 1mm mercury absolute. It is preferable to reduce the pressure much more than to 1 mm mercury absolute. The best results are obtained with an absolute pressure of between about 0.05 mm and 0.2 mm. This latter pressure range is ordinarily readily attainable in both laboratory and commercial freeze-drying apparatus, the design, construction and operation of which are all well known to those skilled in the art. After the pressure of the environment described above has been reduced to an operating level, heat is introduced into such an environment. The temperature of the environment is raised to a point where the maximum sublimation rate can be achieved without melting the frozen mass. As a general rule, the temperature and the pressure are inversely related; the more effective the pressure reduction, the higher the temperature which can be employed in the subliming operation. As a common guide it can be said that a maximum environment temperature of 50° C. can be reached with a highly efficient vacuum system where the absolute pressure is maintained at about 0.05 mm absolute (50 μm). In any event, the temperature should be raised slowly so as to avoid overloading the pressure-reducing system which can produce an undesirable melting of the frozen mass. Preferably, the temperature of the environment in the subliming operation should be maintained between from about 10° C. and about 40° C. with the pressure held at or below 0.2 mm absolute.

Subliming of the ice from the frozen mass is continued until the moisture content of the cefazolin sodium crystals is below 6 percent and the $C_1$–$C_3$ alcohol content is below 1 percent. Such a specification assures physical stability of the resulting crystals. Cefazolin sodium crystallizes as the pentahydrate. Holding the crystals at 25° C. to 30° C., after the ice has been completely sublimed, converts the penta- to the hemihydrate. Such crystals can contain up to about 6 percent moisture.

The cefazolin sodium prepared as detailed above is essentially crystalline. For example, physical analyses of cefazolin sodium hemi-hydrated indicated a crystallinity of greater than 90 percent. In any event, a sufficiently high amount of crystallinity was obtained to impart storage stability; i.e., an absence of a yellowing of the substance and loss of microbiological potency for up to 3 years at room temperature. These cefazolin sodium crystals can be sterile filled into previously sterilized ampoules in appropriate quantities for reconstitution for parenteral administration.

In another aspect of this invention the procedure outlined and discussed in detail hereinbefore is augmented by an additional step which comprises filling a measured volume of the sterile $C_1$–$C_3$ alcohol-water solution from step (b) into a previously sterilized ampoule, such measured volume containing the quantity of cefazolin sodium which is desired in such ampoule after the freeze-drying operation. The ampoules containing the sterile $C_1$–$C_3$ ethanol-water solution of cefazolin sodium are then processed in the same manner as described above. The resulting freeze-dried cefazolin sodium ampoule is ready for sterile stoppering and capping.

In practice it is preferred to sterile fill a measured volume of the sterile $C_1$–$C_3$ alcohol-water solution into a previously sterilized ampoule as at least two beneficial results are obtained. First, a more precise and consistent quantity of the cefazolin sodium can be filled into an ampoule in the liquid form than in the solid (crystals) form. And, second, it is much easier to achieve and maintain sterile operating conditions in liquid filling operations than in dry filling operations. Moreover, air pollution is less of a problem when handling liquids than dry materials.

The instant invention is further illustrated by the following example.

EXAMPLE I

Three hundred and forty-eight grams of cefazolin sodium having a moisture content of about 3.5 percent were dissolved in one liter of water for injection, U.S.P. and the resulting solution was q.s'd. to 1200 ml.

To the 1200 ml. aqueous solution of cefazolin sodium 120 ml. of absolute ethanol were added with vigorous agitation.

The resulting ethanol-water solution of cefazolin sodium was filtered through a 0.45 μm Millipore membrane into an appropriate vessel.

The ethanol-water solution of cefazolin sodium was filled into previously sterilized vials in an amount of about 4.35 ml. per vial. The quantity of solution was calculated to provide 1 gram ampoules of cefazolin sodium with an approximate excess of 7 percent.

The filled vials were placed in a conventional freeze-drying unit and the temperature of the solution was slowly lowered to −10° C. over a period of 3 plus hours and then the temperature was rapidly lowered to below −30° C. as quickly as possible. The vials were held for 1 hour plus after the frozen mass had reached a temperature below −30° C.

The pressure in the freeze-dryer was reduced to below 0.2 mm mercury absolute and the temperature was raised to about 10° C. for the sublimation of the ethanol-water solvent. Eventually the temperature was raised to 25° C. taking care not to melt the frozen mass in the vials. When the sublimation process was completed, the vacuum was released and the resulting vials were tested for moisture content, ethanol content and reconstitution time.

Typical moisture content on individual vials was 2.16, 2.11, 2.05, and 2.24 percent.

Two vials tested for ethanol residue showed 0.42 and 0.45 percent, respectively.

Five vials examined for reconstitution time required between 30 and 60 seconds to dissolve the cefazolin sodium in 2.5 ml of water for injection, U.S.P.

EXAMPLE 2

A 1 g. sample of cefazolin sodium was dissolved in 3 ml. of water, and 1 ml. of 95 percent methanol was added. The solution was placed in an ampoule and freeze-dried following the temperature and pressure sequence used in Example 1. When the process was complete, the dried product was examined microscopically and found to consist of essentially 100 percent crystalline cefazolin sodium.

EXAMPLE 3

One g. of cefazolin sodium was dissolved in 3 ml. of water, and 1 ml. of 95 percent ethanol was added. The freeze-drying procedure of Example 1 was followed again, and the dried product was analyzed microscopically. It was found that the product consisted of approximately 100 percent crystalline cefazolin sodium.

EXAMPLE 4

A solution was made at room temperature of 1 g. of cefazolin sodium in 3 ml. of water. A 1 ml. portion of isopropanol was added, and the solution was freeze-dried according to the scheme of Example 1. The dried product was determined microscopically to comprise substantially 100 percent of crystalline cefazolin sodium.

EXAMPLE 5

A 1 g. portion of cefazolin sodium was dissolved in 3 ml. of water, and 1 ml. of n-propanol was added. The hydro-alcoholic solution was freeze-dried according to the method of Example 1, and the product was analyzed microscopically. It was found to consist of crystalline cefazolin sodium, with substantially no amorphous compound present.

What is claimed is:

1. A method of preparing sterile essentially crystalline cefazolin sodium for reconstitution for parenteral administration comprising the steps of:
   (a) dissolving said cefazolin sodium in a solvent comprised of from about 2 to about 25 percent ethanol and from about 98 to about 75 percent water (v/v);
   (b) filtering the solution from (a) through a sterilizing filter;
   (c) cooling the sterile filtrate from (b) slowly over a period of from 3 to about 12 hours from room temperature to about −10° C.;
   (d) cooling the preparation from (e) rapidly to a temperature of between −30° C. and about −40° C.;
   (e) maintaining the temperature of the preparation from (d) below −30° C. for a period of from 1 to 2 hours;
   (f) reducing the pressure of the environment in which the preparation from (e) is maintained to a maximum of 1 mm of mercury absolute;
   (g) raising the temperature of the environment in which the preparation from (f) is maintained to a maximum of about 50° C., avoiding the melting of such preparation; and
   (h) subliming the solvent from the preparation from (g) until the resulting crystals of said cefazolin sodium have a moisture content of not more than 6.0 percent, and a $C_1$–$C_3$ alcohol content of not more than 1.0 percent.

2. The method according to claim 1 wherein the $C_1$–$C_3$ alcohol content of the $C_1$–$C_3$ alcohol-water solution of cefazolin sodium is from about 2 to about 15 percent (v/v).

3. The method according to claim 1 wherein solvent system contains about 10% ethanol and about 98% water.

4. The method according to claim 1 wherein the concentration of the cefazolin sodium in the $C_1$–$C_3$ alcohol solution is between about 20 and about 40 percent (W/V).

5. The method according to claim 4 wherein the concentration of cefazolin sodium is between about 23 and about 28 percent (W/V).

6. The method according to claim 4 wherein the concentration of cefazolin sodium is about 25 percent (W/V).

7. The method according to claim 1 wherein the pressure is reduced to between about 0.05 and about 0.20 mm of mercury absolute (50 to 200 μm absolute) and the temperature of the environment is raised slowly to between about 0° C. and about 50° C. maintaining an absolute pressure of no more than 0.20 mm. of mercury avoiding the melting of said cefazolin sodium preparation.

8. A method of preparing an ampoule of sterile, essentially crystalline cefazolin sodium for reconstitution of parenteral administration comprising the steps of:
   (a) dissolving said cefazolin sodium in a solvent comprised of from about 2 to about 25 percent of a $C_1$–$C_3$ alcohol and from about 98 to about 75 percent water (v/v);
   (b) filtering the solution from (a) through a sterilizing filter into a previously sterilized container;
   (c) filling a volume of the sterile solution from (b) into a previously sterilized ampoule such that the quantity of solute therein is the amount of said cefazolin sodium desired in said ampoule;

(d) cooling the filled ampoule from (c) slowly over a period of from 3 to about 12 hours from room temperature to about −10° C.;

(e) cooling the ampoule from (d) rapidly to a temperature of between −30° C. and about −40° C.;

(f) maintaining the temperature of the ampoule from (e) below −30° C. for a period of from 1 to about 2 hours;

(g) reducing the pressure of the environment in which the ampoule from (f) is maintained to a maximum of 1 mm of mercury absolute.

(h) raising the temperature of the environment in which the ampoule from (g) is maintained to a maximum of about 50° C., avoiding the melting of the contents of such ampoule; and (i) subliming the solvent from the preparation from (h) until the resulting crystals of said cefazolin sodium have a moisture content of not more than 6.0 percent and a $C_1$-$C_3$ alcohol content of not more than 1.0 percent.

9. The method according to claim 8 wherein the solvent system contains about 10% ethanol and about 90 percent water (v/v).

10. The method according to claim 8 wherein the concentration of the cefazolin sodium in the $C_1$-$C_3$ alcohol-water solution is between about 20 and about 40 percent (W/V).

11. The method according to claim 10 wherein the concentration of cefazolin sodium is between about 23 and about 28 percent (W/V).

12. The method according to claim 10 wherein the concentration of cefazolin sodium is about 25 percent (W/V).

13. The method according to claim 8 wherein the pressure is reduced to between about 0.05 and about 0.20 mm of mercury absolute (50 to 200 μm absolute) and the temperature is raised slowly to between about 0° C. and about 50° C. maintaining an absolute pressure of no more than 0.20 mm of mercury avoiding the melting of said cefazolin sodium preparation.

* * * * *